United States Patent [19]

Ulman

[11] Patent Number: 4,678,527
[45] Date of Patent: Jul. 7, 1987

[54] METHOD FOR MAKING NONPLANAR ABSORBENT PRODUCTS

[75] Inventor: John Ulman, Woodbridge, N.J.

[73] Assignee: Personal Products Company, Milltown, N.J.

[21] Appl. No.: 651,125

[22] Filed: Sep. 17, 1984

[51] Int. Cl.⁴ .............................................. B32B 31/08
[52] U.S. Cl. ................................ 156/213; 156/164; 156/229; 156/251; 156/274.8; 156/275.1; 156/275.3; 156/308.4; 264/32
[58] Field of Search ................ 156/73.5, 164, 212–214, 156/223, 228, 250–251, 258, 261, 263–264, 274.8, 275.1, 275.3, 275.7, 292, 308.2, 308.4, 515, 556, 559, 560, 566–567, 581–582, 583.1, 229; 264/32; 604/384–385, 365

[56] References Cited

U.S. PATENT DOCUMENTS

| | | | |
|---|---|---|---|
| 3,466,214 | 9/1969 | Polk | 156/275.1 |
| 3,575,174 | 4/1971 | Mogor | 604/385 |
| 3,886,941 | 6/1975 | Duane et al. | 604/385 |
| 4,081,301 | 3/1978 | Buell | 156/164 |

Primary Examiner—Donald E. Czaja
Assistant Examiner—Merrell C. Cashion, Jr.
Attorney, Agent, or Firm—Jason Lipow

[57] ABSTRACT

An arcuate shaped body fluid absorbent product is made by a process which employs the steps of delivering onto an arcuate shaped surface a composite comprising a layer of body facing cover material, a layer of absorbent core and a layer of garment facing cover material. The core, sandwiched between the two cover materials, is planar in the relaxed state. The cover materials are sealed together about the periphery of the core while the composite is deformed on the arcuate shaped surface to produce an arcuate shaped product.

11 Claims, 6 Drawing Figures

METHOD FOR MAKING NONPLANAR ABSORBENT PRODUCTS

BACKGROUND OF THE INVENTION

This invention concerns the manufacture of nonplanar product for absorbing body fluids and, in particular, concerns methods for making sanitary napkins and other absorbent products designed to be worn in the perineal area of the body including for example, panty liners, panty shields, incontinence pads, diapers and the like.

Traditionally such products comprise generally planar pads of absorbent materials having, on the side of the product intended to be worn against the body, a body fluid pervious cover adapted to permit the flow of body fluid, e.g., menses or urine, from the body to the absorbent pad. The opposite or garment facing side of the pad is generally provided with a body fluid impervious cover to insure that such body fluid absorbed by the pad does not stain or otherwise flow onto the undergarment of the wearer. When such products are placed against the body and inside the crotch portion of an undergarment they deform and take the arcuate shape of the body with the body facing side of the product being concave and the garment side being convex.

Unfortunately, since the garment side cover of prior products is generally inelastic and hence cannot lengthen, the napkin, in assuming this shape, does so by virtue of having the cover on the body facing side shorten. This shortening is accomplished by forming wrinkles or pleats on the body facing side of the product. To a degree, the absorbent pad also forms wrinkles or pleats on this side of the product. These wrinkles or pleats are highly undesirable in that they cause user discomfort and also create transverse channels allowing body fluid to bypass the product and leak from the longitudinal sides onto the undergarment.

The problem associated with planar body fluid absorbent products is particularly aggravated when the absorbent pad is comprised of a resilient material, i.e., one with elastic memory, such as for example, absorbent polymeric foam. In this instance, the product when placed against the body in conformance with the body contours will then tend to straighten out and return to its original planar shape to the degree that the constraining body and undergarment surfaces will allow. The result is that only a small portion of the product remains in intimate contact with the body with a large portion of the product standing away from the body causing user discomfort, possible failure by leakage and even embarrassing visibility through the user's garments.

Several suggestions already exist in the prior art for providing body fluid absorbent products manufactured in an arcuate shape which tend to obviate the above problems with respect to planar products. Thus, for example, in U.S. Pat. No. 3,236,238 issued to E. A. Morse on Feb. 22, 1966, a curved sanitary napkin is disclosed which incorporates a body facing cover having heat shrinkable elements therein which, upon shrinking, cause the napkin to curve. In U.S. Pat. No. 3,262,451 issued on July 26, 1966 to E. A. Morse, a curved sanitary napkin is disclosed which incorporates, in the absorbent pad, a heat shrinkable element which, upon shrinking, causes the napkin to curve. In U.S. Pat. No. 2,964,039 issued on Dec. 13, 1960 to R. W. Johnson, Jr., et al. a curved sanitary napkin is suggested which comprises a curved, molded, absorbent pad, such pad being stabilized in the curved form. In U.S. Pat. No. 3,445,897 issued to N. J. Franz on May 27, 1969, a method of making a wrapped curved napkin from a preshaped napkin core is disclosed. These prior suggestions have, in the main, failed to be commercialized primarily because they require relatively exotic raw materials or unusual and difficult processing steps, incompatible with the high speed production of the relatively inexpensive products designed to be discarded after a single use.

Accordingly, there is a need for a relatively simple process for manufacturing curved absorbent products to obviate the problems associated with planar products without the complexity and expense inherent in the prior suggestions.

SUMMARY OF THE INVENTION

In accordance with this invention, an arcuate shaped body fluid absorbent product having a concave body facing side and a convex garment facing side is manufactured from materials already suggested or in use in products of this nature and by a simple process readily adaptable to the high speed production mandated by commercial considerations for products of this kind.

Specifically, the process of this invention employs the steps of delivering onto an arcuate shaped surface a composite comprising a first layer of body facing side cover material; a second layer of absorbent core and a third layer of garment facing side cover material. The core, sandwiched between the two layers of cover material is planar in the relaxed state, i.e., in the absence of deforming forces and when laid upon a flat surface. The cover material layers of the composite extend beyond the periphery of the absorbent core and are in face-to-face relationship to each other beyond said periphery. The composite is deformed to conform to the arcuate shape of the arcuate shaped surface and, while the deformed composite is still on the arcuate shaped surface, the two cover materials are then sealed together about the periphery of the absorbent core. Excess cover materials may then be removed by die cutting or the like.

In one embodiment of this invention, the arcuate shaped surface is convex and the composite is delivered thereon with the body facing side cover in face-to-face contact with said arcuate shaped surface. In a second embodiment of this invention, the arcuate shaped surface is concave and the composite is delivered thereon with the garment facing side cover in face-to-face contact with said arcuate shaped surface.

The result is that by sealing the cover material together while the composite is in its deformed and curved configuration, the resulting product remains curved, i.e., the body facing cover is actually shorter than the garment facing cover and this is accomplished without wrinkling. Even in the case where the absorbent originally comprises a resilient material which will exert forces in an effort to return to its planar shape, these forces will be resisted by the sealed together covers and the product will remain in the curved shape. In a preferred embodiment the cover contains thermoplastic materials and the sealing is accomplished by heat sealing. The die cutting may take place at any point in the process after the sealing operation and may even take place essentially contemporaneously with the sealing operation.

DETAILED DESCRIPTION OF THE INVENTION

Figure 1:
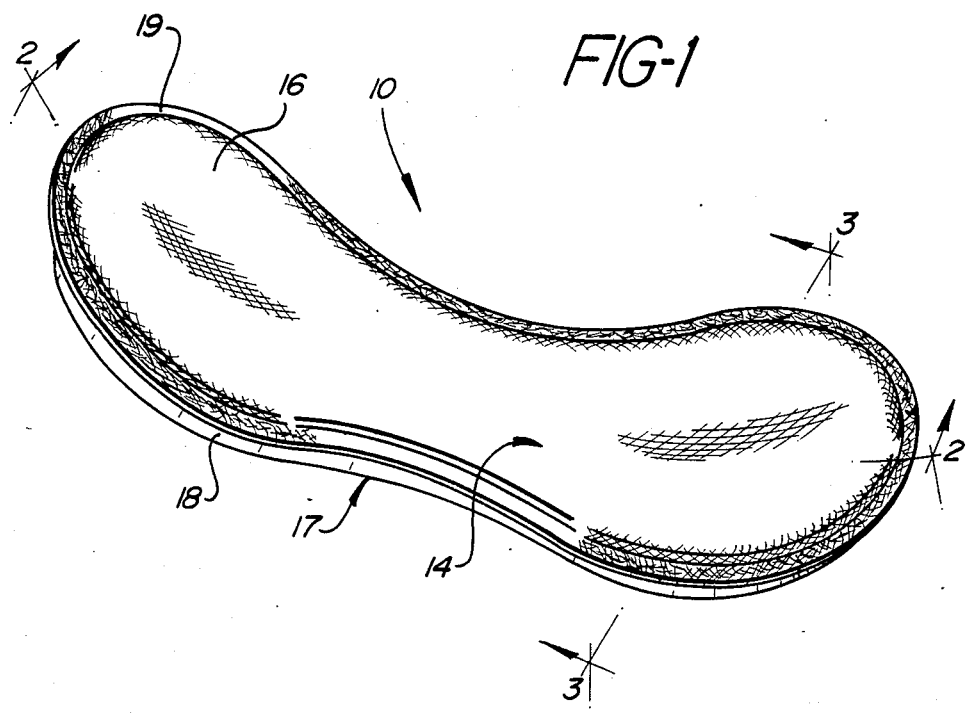
FIG. 1 is a perspective view of an arcuate shaped sanitary napkin made in accordance with the teachings of this invention.
Figure 2:
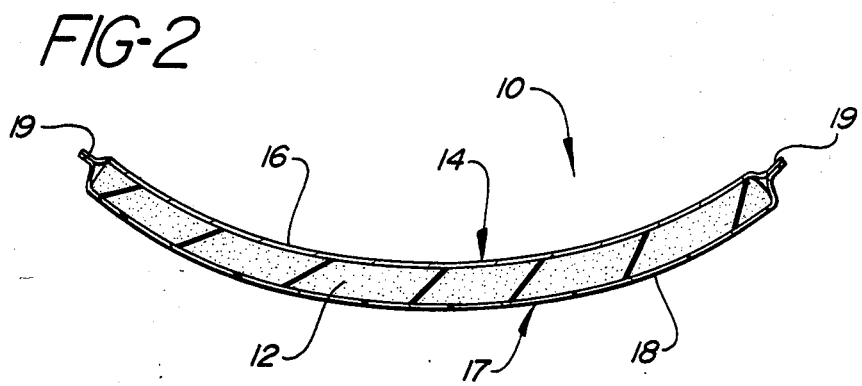
FIG. 2 is a longitudinal cross-sectional view of the napkin of FIG. 1 taken through line 2—2.
Figure 3:
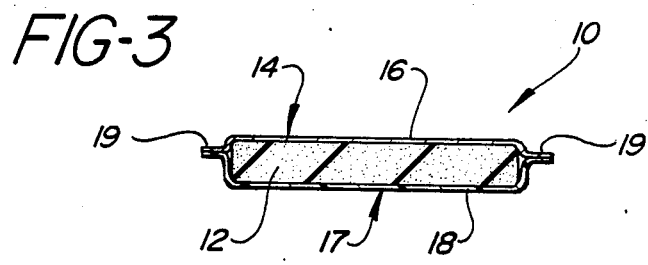
FIG. 3 is a transverse cross-sectional view of the napkin of FIG. 1 taken through line 3—3.

Referring now to FIGS. 1-3, illustrated there in perspective, longitudinal cross-sectional and transverse cross-sectional views, respectively, is an arcuate sanitary napkin 10 made in accordance with the teachings herein. Napkin 10 consists of an absorbent pad 12 comprising any of the materials suitable for use in body fluid absorbent products such as, for example, loosely associated absorbent materials such as cellulose fibers, e.g., wood pulp, regenerated cellulose or cotton fibers. Such fibers may be chemically or physically modified and the pad may include such fibers in combination with other materials, both natural and synthetic such as hydrophilic foams, other hydrophilic polymers or the like. The absorbent pad may also consist in whole or in part of a layer or layers of resilient material such as polymeric foams or resilient fibrous layers. These resilient materials need not be hydrophilic provided, of course, that they are combined with other hydrophilic materials but they may also be materials normally hydrophobic which have been treated to have hydrophilicity.

The body facing side 14 is covered with a layer of body fluid pervious material to form the body facing cover 16. The cover 16 may be any woven or nonwoven material pervious to body fluid striking its surface, such covers being well known in the art and being comprised of rayon, cotton, synthetic fibers or the like. In a preferred embodiment, the cover comprises thermoplastic material capable of being fusibly sealed to another element of the napkin, e.g., by heat, pressure, sonic sealing, or the like.

A material of choice for the cover is a fabric comprising heat bondable polyester/polyethylene conjugate fibers. Such conjugate fibers are fibers which comprise a polyester core surrounded by a sheath of polyethylene. Preferably, the conjugate fibers employ high density polyethylene, that is, linear polyethylene that has a density of at least 0.94 gm/cc and a Melt Index (as determined by ASTM D-1288E method, employing the parameters of 190° C. and 2160 gms) of greater than 1, preferably greater than about 10, and more preferably from about 20 to about 50. The fibers may comprise from about 40 to about 60 percent, by weight, polyester and preferably, from about 45 to 55 percent by weight polyester, with the remainder being polyethylene. Such fibers may be used in deniers of from 1 to about 6 and may be from about ½ inch (1.27 cm) to about 4 inches (10.16 cm) long. The fabric comprising such fibers is stabilized by applying heat thereto under essentially zero pressure whereby thermal bonding takes place without destroying the integrity of the fibers.

Still another material useful as the body facing cover is an apertured film such as a netlike apertured film of polyethylene.

Overlying the second major surface 17 of the pad 12 is a body fluid impervious layer 18. The layer 18 is provided to preclude body fluid from passing onto an undergarment and may be constructed of any material suitable for this purpose. For example, the layer 18 may be a polymeric film such as polyethylene, polypropylene, or may be a normally fluid pervious material that has been treated to be impervious such as a fluid repellant paper. Advantageously, the layer 18 is a heat bondable material such as polyethylene which can be bonded to layer 16 to completely enclose pad 12.

Irrespective of the materials of construction the layers 16 and 18 are sealed together about the periphery of the pad 12 to form flange 19. Such sealing may be accomplished by heat and/or pressure in the case of heat bondable materials. Alternatively such sealing may be accomplished by use of adhesives such as cold emulsion adhesives or hot melt adhesives.

As can be best viewed in FIGS. 1 and 2, the napkin 10 has nonplanar shape, being arcuate in the longitudinal direction; concave with respect to the body facing side and convex with respect to the garment facing side. As viewed in FIG. 3, the napkin 10 is not arcuate in the transverse direction, although it will be understood that the teachings of this invention are applicable to napkins that are arcuate in the transverse direction as well.

Figure 4:
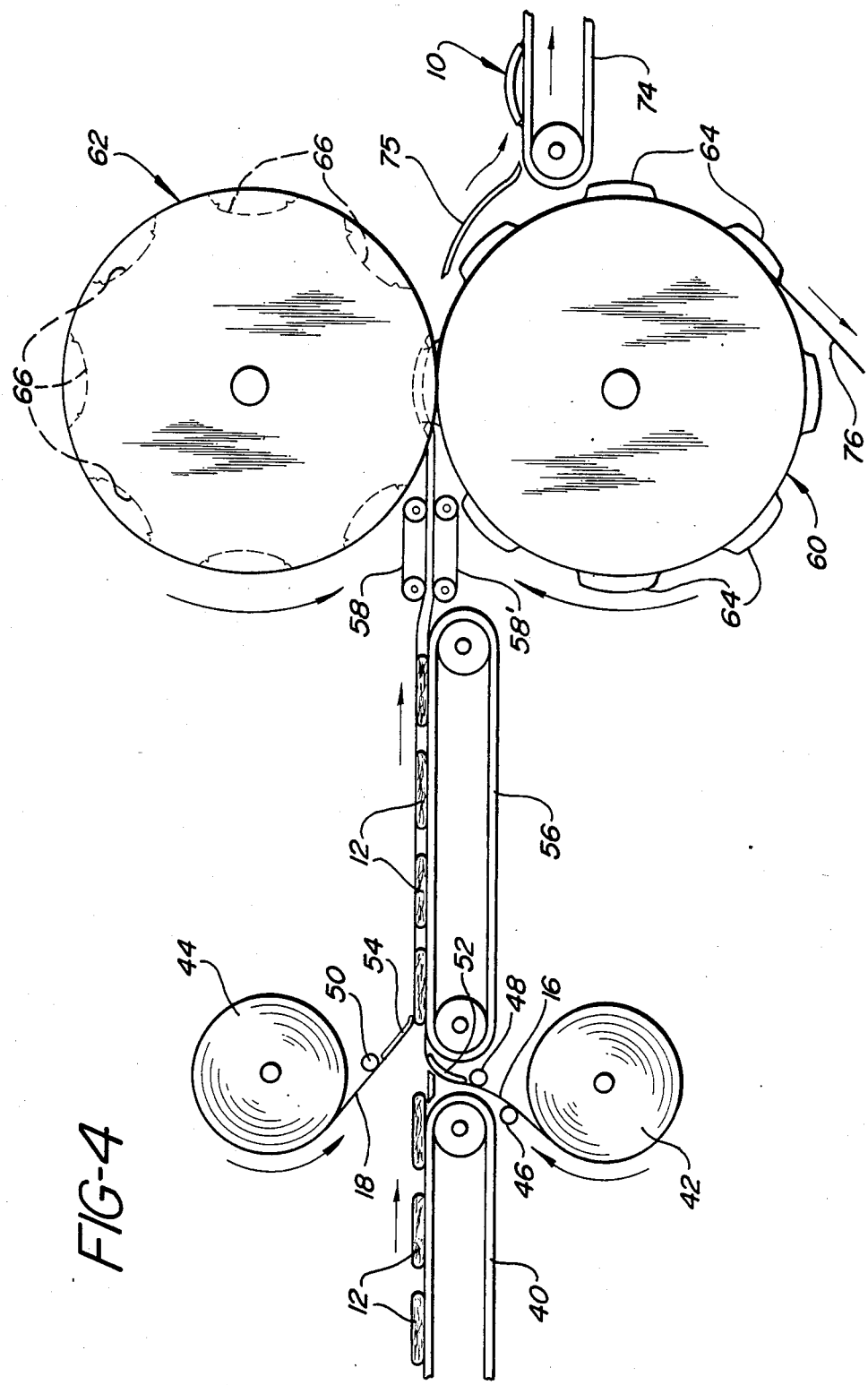
FIG. 4 is a schematic side elevational view of a production line utilizing the teachings of this invention.
Figure 5:
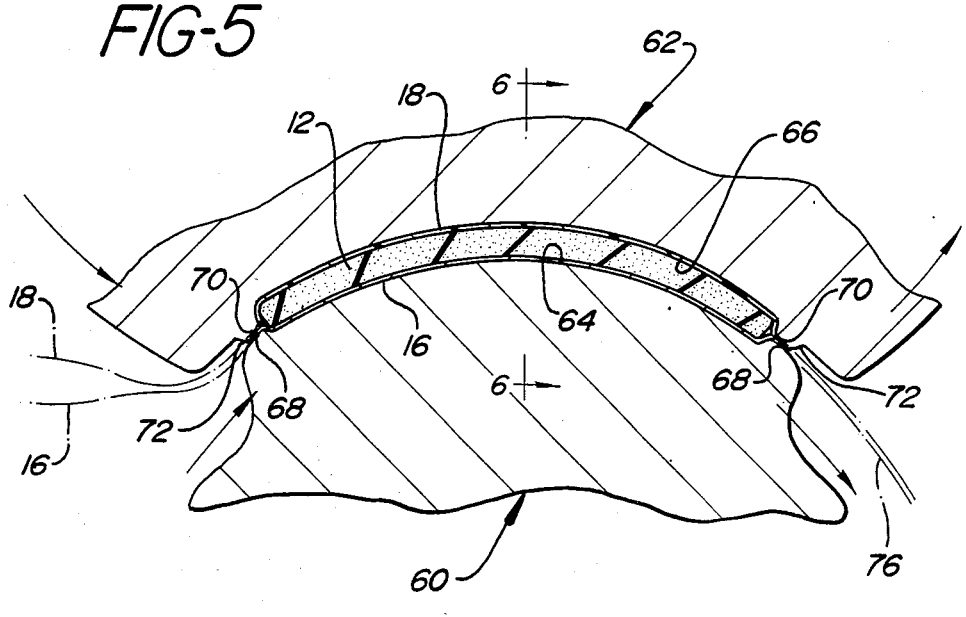
FIG. 5 is an enlarged cross-section of a napkin being cut and sealed while in the anvil and cutting rollers of FIG. 4, taken through the longitudinal center line of the napkin.
Figure 6:
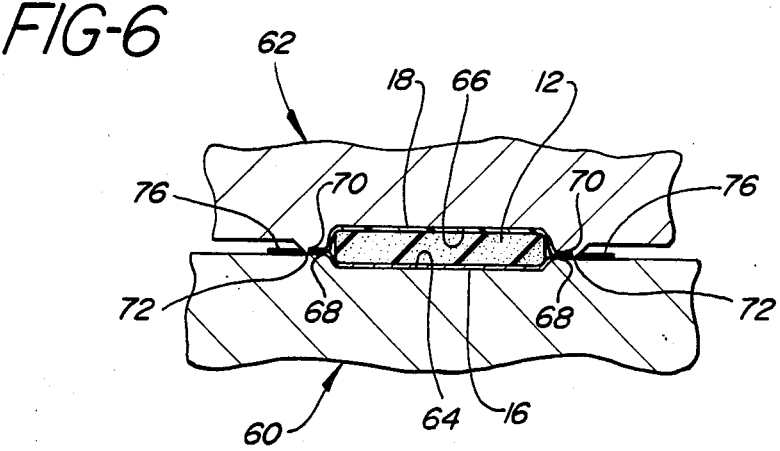
FIG. 6 is a transverse cross-sectional view of FIG. 5, taken through line 6—6.

FIGS. 4-6 schematically illustrate, in side elevational view, enlarged longitudinal cross-sectional view, and in transverse cross-sectional view, apparatus for carrying out the process of this invention.

Referring to FIG. 4, an endless belt 40 carries planar pads 12 in the machine direction, as indicated by the arrow, toward a junction station with body facing cover material 16 and garment facing cover material 18. Pads 12 may be formed by a variety of methods known in the art. For example, if pads 12 comprise wood pulp fluff, such pads may be formed by forming a long snake of wood pulp fluff from pulp board in a hammer mill and separating such snake into individual pads. If pads 12 comprise hydrophilic foam, such pads may be die cut from a long strip of such foam or may be individually molded during the foam forming process.

The pads 12 are sandwiched between the two cover materials supplied from cover supply rolls 42 and 44 after such cover material has passed control rollers 46, 48 and 50 as well as directing plates 52 and 54. The cover material is extensive enough to be wider than the pads 12 so as to extend completely around the periphery of pads 12 when pads 12 are sandwiched therebetween.

The composite of cover and pad is carried in the machine direction on endless belt 56 and via feed belts 58, 58', to the nip of anvil roller 60 and seal roller 62. Anvil roller 60 is provided with a plurality of circumferentially spaced arcuate surfaces 64 adapted to cooperate with correspondingly shaped pockets 66 in seal roller 62.

As best viewed in FIGS. 5-6, when the pad 12, sandwiched between the cover material 16 and 18, is delivered onto the arcuate surface 64, pocket 66 cooperates with arcuate surface 64 to deform the normally planar pad 12 into the shape of arcuate surface 64. Surfaces 68 on arcuate surface 64 and surfaces 70, in seal roller 62 adjacent to pocket 66, cooperate to seal the cover materials 16 and 18 together around the periphery of the pad 12 while the pad 12 is in the deformed state. Preferably when cover material 16 and 18 comprise heat sealable material, this sealing is accomplished by heating either surfaces 68, surfaces 70 or both. Alternatively, it is possible to provide adhesive material (either cold emulsion adhesive or hot melt adhesive) to either or both of these cover materials in the area in which they are in face-to-face contact between surfaces 68 and 70. Such adhesive could be supplied at a point in the process between each of the supply rolls 44 or 42 and the endless belt 56.

In still another preferred embodiment, the surface 70 is provided with a knife edge 72 adapted to cut away excess cover material and separate the sealed together composite into individual pads. It is, of course, possible to provide such knife edge on surface 68.

Referring back again to FIG. 4, the process is continued by passing the now separated arcuate napkin 10 onto endless belt 74 for further handling (e.g., packaging) and removing the waste portion 76 of the cover material.

I claim:

1. A process for producing an arcuate shaped napkin having a concave body facing side and a convex garment facing side comprising:
   delivery onto an arcuate shaped surface, a composite comprising a layer of absorbent core, said layer of absorbent core having a body facing side and a garment facing side; said composite further comprising a first layer of body facing side cover overlying said body facing side of said absorbent core and a second layer of garment facing side cover overlying said garment facing side of said absorbent core;
   said cover layers extending beyond the periphery of said absorbent core and being in face-to-face relationship to each other beyond said periphery and being unsealed to each other so as to be free to move relative to each other while still maintaining their face-to-face relationship;
   deforming said composite to conform to the arcuate shape of the arcuate shaped surface; and
   sealing said cover layers to each other about the periphery of said absorbent core while said composite is on said arcuate shaped surface.

2. The process of claim 1 wherein said covers comprise heat sealable material and said sealing is heat sealing.

3. The process of claim 1 wherein adhesive is deposited between said covers and said sealing is adhesive sealing.

4. The process of claim 3 wherein said adhesive is a hot melt adhesive.

5. The process of claim 3 wherein said adhesive is an emulsion adhesive.

6. The process of claim 1 wherein said deforming and sealing steps are performed in a single step.

7. The process of claim 1 wherein excess cover is cut from said sealed composite.

8. The process of claim 7 wherein said sealing and cutting steps are performed together.

9. The process of claim 8 wherein said deforming, sealing and cutting steps are performed together.

10. The process of claim 1 wherein said arcuate shaped surface is convex and said composite is delivered with said body facing side cover in face-to-face contact with said arcuate shaped surface.

11. The process of claim 1 wherein said arcuate shaped surface is concave and said composite is delivered with said garment facing side cover in face-to-face contact with said arcuate shaped surface.

* * * * *